US00PP14539P29

(12) United States Plant Patent
van Marrewijk

(10) Patent No.: US PP14,539 P2
(45) Date of Patent: Feb. 17, 2004

(54) PETUNIA PLANT NAMED 'HORPUVA'

(50) Latin Name: *Petunia x hybrida*
Varietal Denomination: Horpuva

(76) Inventor: Wim C. J. van Marrewijk, Carderie 23, Maassluis (NL), 3142 BA ( * ) Notice: Subject to any disclaimer, the term of this patent is extended or adjusted under 35 U.S.C. 154(b) by 0 days.

(21) Appl. No.: 10/125,912

(22) Filed: Apr. 19, 2002

(51) Int. Cl.[7] ..... A01H 5/00
(52) U.S. Cl. ..... Plt./356
(58) Field of Search ..... Plt./356

(56) References Cited

PUBLICATIONS

UPOV–Rom hit on 'Horpuva', Plant Variety Database 2002/05.*

* cited by examiner

*Primary Examiner*—Anne Marie Grunberg

(57) ABSTRACT

A new cultivar of Petunia plant named 'Horpuva' that is characterized by variegated light green leaves, with irregular cream-yellow margins, a trailing habit, and large brilliant purple flowers. In combination these traits set 'Horpuva' apart from all other existing varieties of Petunia known to the inventor.

2 Drawing Sheets

Genus: Petunia.
Species:×hybrida.
Denomination: Horpuva.

BACKGROUND OF THE INVENTION

The present invention relates to a new and distinct cultivar of Petunia grown for use as an ornamental container plant. The new cultivar is known botanically as Petunia ×hybrida and will be referred to hereinafter by the cultivar name 'Horpuva'.

'Horpuva' exhibits a trailing habit and is a branch sport of the parent plant Petunia 'Shihi Purple'. The new cultivar was discovered by the inventor in a cultivated area of Naaldwijk, The Netherlands in February 1998. The inventor produces rooted cuttings and selected 'Horpuva' from a crop of the parent plant Petunia 'Shihi Purple' (unpatented). The selection was made based on the variegated light green leaves with cream-yellow margins. The inventor took six cuttings and planted these for further observation. During April of 1998 the shoots from these cuttings were one hundred percent variegated. The plants are strongly vigorous and by May had produced flowers. During the following summer and fall the inventor produced 600 vegetative cuttings from the original six plants. From these cuttings, resulted a larger crop during the winter and spring of 1999. The European application was made in 1999 but no plants were sold until May 2001.

The closest comparison plant is Petunia 'Limelight' (unpatented). 'Horpuva' is distinguishable from 'Limelight' in flower color, flower size, strong vigor, resistance to cold temperatures, and strong leaves. The parent plant 'Shihi Purple' exhibits non-variegated green foliage. 'Horpuva' is distinguishable from the parent plant by variegated foliage. It is suitable for hanging baskets and containers and performs best in full sunlight, The first asexual reproduction of 'Horpuva' conducted by the inventor in a cultivated area of Naaldwijk, The Netherlands in March 1998. The method used for asexual propagation was vegetative cuttings. The characteristics of the new cultivar have been determined stable and are reproduced true to type in successive generations.

SUMMARY OF THE INVENTION

The following traits have been repeatedly observed and represent the characteristics of the new Petunia cultivar 'Horpuva'. These traits in combination distinguish 'Horpuva' from all other commercial varieties known to the inventor. 'Horpuva' has not been tested under all possible conditions and phenotypic differences may be observed with variations in environmental, climatic and cultural conditions.

1. Petunia 'Horpuva' exhibits a trailing habit.
2. Petunia 'Horpuva' exhibits variegated light green foliage with irregular cream-yellow margins.
3. Petunia 'Horpuva' exhibits large, brilliant deep purple flowers with darker purple colored veins.
4. Petunia 'Horpuva' is 40–50 cm. in width and 20 cm. in height at maturity.
5. Petunia 'Horpuva' is propagated by vegetative cuttings.
6. Petunia 'Horpuva' is an ornamental suitable for containers and hanging baskets.
7. Petunia 'Horpuva' a strongly vigorous.
8. Petunia 'Horpuva' is hardy to 22° Centigrade.

BRIEF DESCRIPTION OF THE DRAWINGS

The accompanying color drawings illustrate the overall appearance of the new cultivar 'Horpuva' showing the colors as true as it is reasonably possible to obtain in colored reproductions of this type. Colors in the photograph may further differ from the color values cited in the detailed botanical description, which more accurately describe the actual colors of the new variety 'Horpuva'. The drawing on sheet 1 illustrates the entire plant in bloom from a side perspective. The drawing on sheet 2 is a close-up view of the flower and leaves. The drawings were made in April of an 8-week-old plant grown under glass in Lompoc, Calf. in a 14-centimeter container. The drawings were made using conventional techniques and although colors may appear different from actual colors due to light reflectance they are as accurate as possible by conventional photography.

BOTANICAL DESCRIPTION OF THE PLANT

The following is a detailed description of 'Horpuva' as grown in 14-centimeter containers under glass in Lompoc, Calif. The color determinations are in accordance with the 2001 Royal Horticultural Society Color Chart of The Royal Horticultural Society, London, England, except where general color terms of ordinary dictionary significance are used. Growing conditions, diseases and pests are similar to that of other Petunia. There are no growing problems known to the inventor.

Botanical classification: Petunia 'Horpuva'.

Species:×hybrida.

Commercial classification: The new cultivar serves as a perennial in mild climates and as a spring, summer annual in colder climates.

Use: Ornamental for hanging baskets and containers.

Cultural requirements: Performs best in full sunlight with moderate to regular water and well-drained rich compost soil.

Parentage: Petunia 'Horpuva' is a branch sport of the parent plant Petunia 'Shihi Purple'.

Plant description:

*Bloom period.*—Spring, summer.
*Plant habit.*—Trailing habit.
*Vigor.*—Strong vigorous.
*Sexuality.*—Perfect.
*Plant dimensions.*—40–50 cm. in width and 20 cm. in height at maturity.
*Hardiness.*—Hardy to 22° Centigrade.
*Root system.*—Fine.
*Propagation.*—Propagation is accomplished using vegetative cuttings.
*Time to develop roots.*—12–14 days are needed for an initial cutting to develop roots.
*Crop time.*—8 weeks are needed to produce a finished 14-centimeter container from a rooted cutting.

Stem:

*Shape.*—Cylindrical
*Young stem color.*—166A.
*Mature stem color.*—145A.
*Mature stem dimensions.*—64 cm. in length and 5 mm. in diameter.
*Young stem dimensions.*—12 cm. in length and 3 mm. in width.
*Stem surface.*—Stipitate glandular.
*Internode lenght.*—0.75 cm. between nodes.

Foliage:

*Type.*—Evergreen.
*Arrangement.*—Leaves are alternate and spirally arranged on stems.
*Shape.*—Ovate.
*Division.*—Simple.
*Apex.*—Acute.
*Base.*—Cuneate.
*Venation pattern.*—Pinnate with depressed veins on the adaxial surface and protruding on veins on the abaxial surface.
*Vein color* (*abaxial and adaxial surfaces*).—147A.
*Young leaf dimensions.*—2.5 cm. in length and 1.5 cm. in width.
*Mature leaf dimensions.*—6.5 cm. in length and 3.5 cm. in width.
*Leaf margins* (*young and mature*).—Entire and sinuous.
*Texture.*—Soft and flexible.
*Attachment.*—Petiolate.
*Petiole dimensions.*—6 mm. in length and 3 mm. in width.
*Petiole surface.*—Stipitate glandular.
*Leaf surfaces* (*adaxial and abaxial*).—Stipitate glandular.
*Young and mature leaf color* (*adaxial and abaxial surfaces*).—Center is 147B and margin is 150D.
*Fragrance.*—Absent.

Flowers:

*Inflorescence type.*—Solitary.
*Shape.*—Funnelform.
*Flower dimensions.*—7.5 cm. in diameter and 6.5 cm. in height.
*Persistent or self-cleaning.*—Self-cleaning.
*Aspect.*—Facing upward.
*Bud dimensions.*—5.50 cm. in length and 1.75 cm. in width.
*Bud shape.*—Obovate.
*Bud color.*—N77A.
*Corolla depth.*—18 mm. in depth.
*Outer surface of corolla.*—Manicate.
*Color of corolla* (*inner surface*).—N77A.
*Color of corolla* (*outer surface*).—N77B.
*Petals.*—Five in number.
*Petal color* (*newly opened upper surface*).—The color is 61A. The brilliant quality of the color is not evident in the drawings or in the color chart reading.
*Petal color* (*mature upper surface*).—A combination of N74A and 72A. The vibrant quality of the colors is not evident in the drawings or in the color chart readings.
*Color of darker veins in petals.*—N77A.
*Petal surfaces.*—Glabrous.
*Petal color* (*lower surface of newly opened and mature petals*).—72B.
*Fused or unfused.*—Fused petals.
*Petal margin.*—Entire and sinuous.
*Calyx color.*—N77C at base.
*Sepals.*—Five in number.
*Sepal dimensions.*—2 cm. in length and 1 cm. in width.
*Sepal margin.*—Sinuous and revolute.
*Sepal surface.*—Stipitate glandular.
*Sepal color.*—The majority of surface area is 145C with the base of the sepal N77C and the margins 141B.
*Peduncle dimensions.*—3 cm. in length and 2.5 mm in width.
*Peduncle surface.*—Pubescent.
*Peduncle shape.*—Cylindrical.
*Flower fragrance.*—Slightly sweet.

Reproductive organs:

*Stamens.*—Six in number.
*Stamen color.*—145D.
*Stamen dimensions.*—The width of the stamens is 1 mm. and the length ranges from 15–18 mm.
*Anther color.*—N77C.
*Anther dimmensions.*—1.50 mm. in width and 1.75 mn. in length.
*Anther shape.*—Made up of four lobes arranged tightly together creating an ovate shaped anther.
*Pollen color.*—N77C.

*Amount of pollen.*—Large amount.
*Pistil.*—One.
*Pistil dimensions.*—18 mm in length and 1 mn. in width.
*Pistil color.*—155A.
*Style dimensions.*—15 mm. in length and 1 mm, in width.
*Style color.*—155A with purple shading N77C toward apex.
*Stigma shape.*—Truncate.
*Stigma color.*—141C.
*Stigma surface.*—Glossy and viscid.
*Stigma dimensions.*—2.5 mm. in diameter and 2 mm. in length.
*Ovary position.*—Superior.
*Ovary color.*—The majority of the ovary surface area is 145B. The base of the ovary is 153C.
*Ovary shape.*—Pointed cone shape.
*Ovary dimensions.*—4 mm. in height and 3 mm. in diameter.

Seed production: No seed production has been observed to date.

I claim:

1. A new and distinct cultivar of Petunia plant named 'Horpuva' as described and illustrated herein.

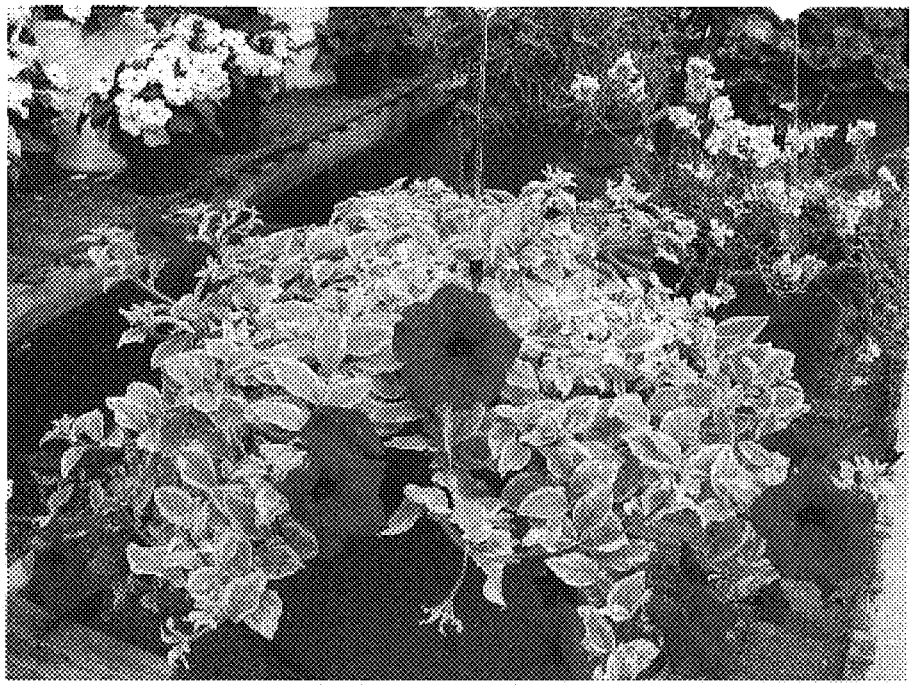

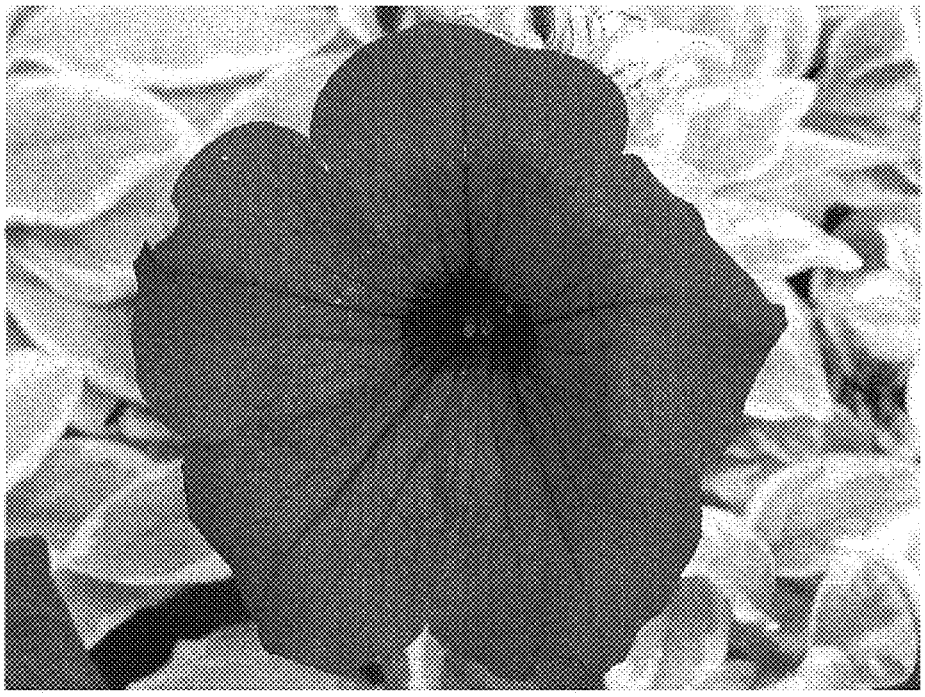

* * * * *